United States Patent
Bense et al.

(10) Patent No.: US 10,495,546 B2
(45) Date of Patent: Dec. 3, 2019

(54) METHOD, SYSTEM AND COMPUTER PROGRAM FOR THE ACOUSTIC ANALYSIS OF A MACHINE

(71) Applicant: Snecma, Paris (FR)

(72) Inventors: William Bense, Melun (FR); Jérôme Lacaille, Rosny sous Bois (FR); Valerio Gerez, Yerres (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 429 days.

(21) Appl. No.: 15/028,284

(22) PCT Filed: Oct. 9, 2014

(86) PCT No.: PCT/FR2014/052556
§ 371 (c)(1),
(2) Date: Apr. 8, 2016

(87) PCT Pub. No.: WO2015/052438
PCT Pub. Date: Apr. 16, 2015

(65) Prior Publication Data
US 2016/0238486 A1    Aug. 18, 2016

(30) Foreign Application Priority Data
Oct. 11, 2013   (FR) ...................... 13 59897

(51) Int. Cl.
*G01M 15/14* (2006.01)
*G01N 29/14* (2006.01)
(Continued)

(52) U.S. Cl.
CPC ............ *G01M 15/14* (2013.01); *G01N 29/14* (2013.01); *G01N 29/4436* (2013.01);
(Continued)

(58) Field of Classification Search
CPC ...... G01M 15/12; G01M 15/14; G01N 29/14; G01N 29/4436; G01N 29/4454;
(Continued)

(56) References Cited

U.S. PATENT DOCUMENTS 5,309,378 A * 5/1994 Beierle ............... G01M 13/028
                                                      700/280
5,918,223 A * 6/1999 Blum ................ G06F 17/30017
(Continued)

FOREIGN PATENT DOCUMENTS

DE    102012105414 A1    12/2012
EP    2538034 A2         12/2012

OTHER PUBLICATIONS

Avery Li-Chun Wang, "An Industrial-Strength Audio Search Algorithm", Shazam Entertainment, Ltd. dated 2003.
(Continued)

*Primary Examiner* — Davetta W Goins
*Assistant Examiner* — Daniel R Sellers
(74) *Attorney, Agent, or Firm* — Pearne & Gordon LLP

(57) ABSTRACT

A method for the acoustic analysis of a machine (M) including the acquisition of at least one acoustic signal supplied by at least one microphone (7) positioned in the machine, characterized in that it comprises the following steps: separation of at least one acoustic signal into a plurality of sound sources, the signal being modelled as a mixture of components, each one corresponding to a sound source; for at least one separated sound source, determination of a characteristic acoustic signature; comparison of at least one characteristic acoustic signature with at least one reference acoustic signature recorded in a reference database (5).

12 Claims, 2 Drawing Sheets

(51) Int. Cl.
  *G01N 29/44* (2006.01)
  *H04R 29/00* (2006.01)

(52) U.S. Cl.
  CPC ....... *G01N 29/4454* (2013.01); *H04R 29/005* (2013.01); *G01N 2291/2693* (2013.01); *H04R 2499/13* (2013.01)

(58) Field of Classification Search
  CPC ................ G01N 29/449; G01N 29/46; G01N 2291/2693; H04R 29/00; H04R 29/005; H04R 2499/13
  USPC .......................................................... 381/56
  See application file for complete search history.

(56) References Cited

U.S. PATENT DOCUMENTS

| | | | |
|---|---|---|---|
| 2002/0165676 A1* | 11/2002 | Wu | G01H 3/125 702/39 |
| 2004/0015251 A1* | 1/2004 | Hamada | G01M 15/12 700/94 |
| 2004/0034482 A1* | 2/2004 | Gross | G01H 1/003 702/39 |
| 2007/0255563 A1* | 11/2007 | Dooley | F02D 41/22 704/236 |
| 2009/0091441 A1 | 4/2009 | Schweitzer | |
| 2010/0033313 A1* | 2/2010 | Keady | G08G 1/0965 340/438 |
| 2010/0139403 A1 | 6/2010 | Liang | |
| 2010/0161255 A1 | 6/2010 | Mian | |
| 2012/0027217 A1* | 2/2012 | Jun | H04S 7/30 381/58 |
| 2012/0148400 A1 | 6/2012 | Gerez | |
| 2012/0327745 A1 | 12/2012 | Yardibi | |
| 2012/0330495 A1* | 12/2012 | Geib | F01D 21/003 701/29.6 |
| 2013/0211768 A1 | 8/2013 | Gerez | |
| 2013/0239653 A1 | 9/2013 | Nicq | |
| 2013/0325286 A1 | 12/2013 | Lacaille | |
| 2014/0299744 A1 | 10/2014 | Rostaing | |
| 2015/0120214 A1 | 4/2015 | Gouby | |
| 2015/0177101 A1 | 6/2015 | Gerez | |
| 2015/0287249 A1 | 10/2015 | Lacaille | |
| 2016/0054233 A1 | 2/2016 | Bense | |
| 2016/0103038 A1 | 4/2016 | Lacaille | |
| 2016/0186890 A1 | 6/2016 | Bense | |
| 2016/0240017 A1 | 8/2016 | Lacaille et al. | |

OTHER PUBLICATIONS

French Search Report issued in application No. FR 1359897 dated Jul. 25, 2014.
International Search Report issued in application No. FR2014/052556 dated Feb. 25, 2015.
Jingchun Zhang, "Research on Motor Fault Diagnosis Based on Blind Source Separation and Wavelet Analysis", Chinese Doctoral Dissertations & Master's Theses Full-text Database (Master), dated 2006.
Hua GE, "The Study of the Blind Source Separation Based on TIFROM Method", Chinese Master's Theses Full-text Database information Science and Technology, pp. 1136-1154, No. 9, 2009—Publication date: Sep. 30, 2009.

* cited by examiner

METHOD, SYSTEM AND COMPUTER PROGRAM FOR THE ACOUSTIC ANALYSIS OF A MACHINE

TECHNICAL FIELD

The invention pertains to the field of monitoring of a machine, for example an engine such as an aircraft engine. In particular, the invention relates to a method and a system for the acoustic analysis of a machine to detect therein or to forecast therein anomalies.

STATE OF THE PRIOR ART

A machine is a mechanical system subjected to stresses which can lead to wear of its components. It is thus sought, generally speaking, to monitor as efficiently as possible the state of a machine to detect or to predict the appearance of defects.

If a machine, for example an aircraft engine, has the drawback of generating noise, it is nevertheless possible to imagine using said drawback to carry out a diagnosis or a prognosis of defects in a non-intrusive manner.

Thus a system for monitoring an airplane turbojet engine is known from the publication US 2007/0255563 A1 according to which acoustic signals stemming from the turbojet engine in operation are recorded using two microphones positioned underneath the nacelle of the turbojet engine, and the acquired signals are compared with reference signals using a voice recognition algorithm. In this way it is possible to identify "words" representative of the state of the turbojet engine among the acquired signals.

Although such a system has the advantage of using proven voice recognition algorithms, its efficiency nevertheless remains limited. Since noise sources are effectively multiple on a turbojet engine, the acquired acoustic signals to analyze are relatively complex and the "words" representative of a defect can considerably vary in amplitude, phase and/or frequency. It is thus not easy to identify such representative "words", and there thus exists a risk of not managing to identify that an acquired acoustic signal is indeed representative of a given defect, notably when a "word" stemming from the acquired acoustic signals differs too considerably from a "word" of the reference signals.

DESCRIPTION OF THE INVENTION

The objective of the invention is to propose a technique making it possible to improve the diagnosis or the prognosis of defects of a machine from an analysis of the noise generated by the machine. It proposes to this end a method for the acoustic analysis of a machine including the acquisition of at least one acoustic signal supplied by at least one microphone positioned in the machine, characterized in that it further comprises the following steps:
- separation of at least one acoustic signal into a plurality of sound sources, said signal being modelled as a mixture of components, each one corresponding to a sound source;
- for at least one of the separated sound sources, determination of a characteristic acoustic signature;
- comparison of at least one characteristic acoustic signature with at least one reference acoustic signature recorded in a reference database.

Certain preferred but not-limiting aspects of this method are the following:
- the reference acoustic signature(s) may each correspond to an acoustic signature characteristic of a defect of the machine, and the method includes an identification of a defect of the machine when a difference between a characteristic acoustic signature of a separated sound source and the reference acoustic signature characteristic of said defect is below a threshold;
- the method may include a step for determining at least one reference acoustic signature, said step comprising:
  - an acquisition of at least one reference acoustic signal supplied by at least one microphone positioned in at least one reference machine;
  - a separation of at least one reference acoustic signal into a plurality of reference sound sources;
  - for at least one of the separated reference sound sources, a determination of a characteristic acoustic signature;
  - a recording in the reference database of the characteristic acoustic signature of at least one separated reference sound source;
- at least one reference machine may be a defect-free machine;
- at least one reference machine may be the same machine considered earlier or a machine of the same type having the same operating history;
- at least one reference machine may include at least two machines.

The subject matter of the invention is also a system for the acoustic analysis of a machine, including means for acquiring at least one acoustic signal supplied by at least one microphone positioned in the machine, and a reference database in which is recorded at least one reference acoustic signature, characterized in that it further comprises a module for separating sources, a module for determining an acoustic signature and a module for comparing acoustic signatures configured for the implementation of the method according to the invention.

And the subject matter of the invention is also a computer program product including code instructions for the execution of the steps of the method according to the invention, when said program is run on a computer.

BRIEF DESCRIPTION OF THE DRAWINGS

Other aspects, aims, advantages and characteristics of the invention will become clearer on reading the following detailed description of preferred embodiment forms thereof, given by way of non-limiting example, and made with reference to the appended drawings in which.

DETAILED DESCRIPTION OF PARTICULAR EMBODIMENTS

Figure 1:
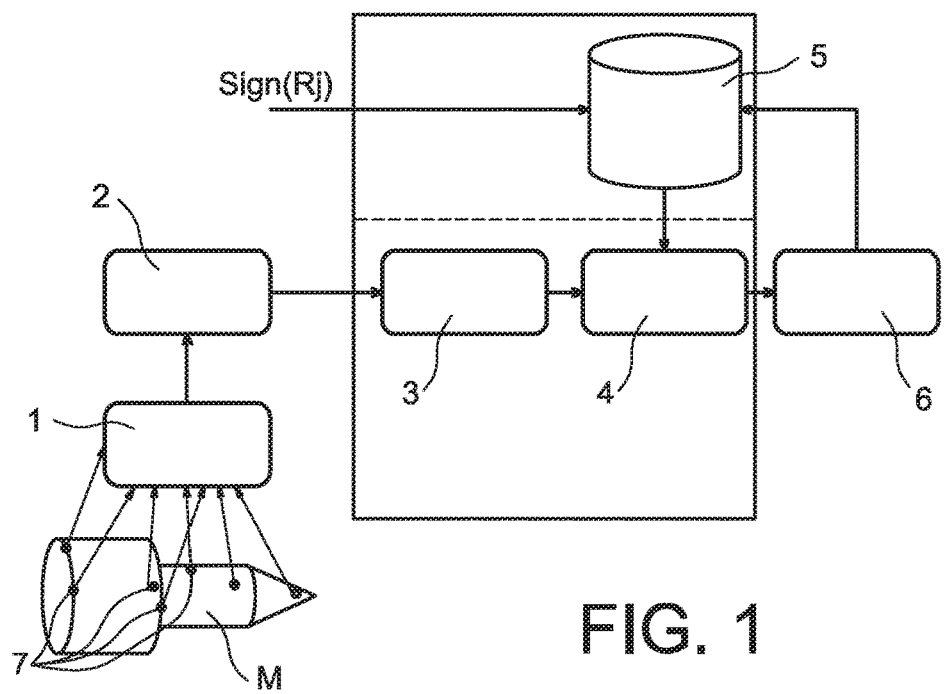
FIG. 1 illustrates in a schematic manner an example of material means implemented in the system or method for the acoustic analysis of a machine according to a first possible embodiment of the invention.

The invention proposes a method, a system and a computer program product making it possible to detect or to forecast defects of a machine via an analysis of the noise generated by the machine. Generally speaking, the invention traces characteristic acoustic signatures using a recognition algorithm implemented, not on the recordings of the noise generated by the machine, but on signals resulting from a breakdown of said recordings into sound sources of said recordings.

FIGS. 1 to 4 illustrate examples of material means implemented in different possible embodiments of the system and method for the acoustic analysis of a tested machine M, in accordance with possible embodiments of the invention. In these figures, common elements bear the same references.

The tested machine M may be an engine of an aerial or land vehicle, for example an aircraft engine as schematically illustrated in FIGS. 1-4. The invention is not however limited to such an illustrative example, but extends in a general manner to the study of any mechanical system generating noise.

At least one microphone 7 is positioned in the machine M, for example underneath the nacelle of an aircraft engine. Preferably a plurality of microphones, for example ten or so microphones, are used which makes it possible notably to spread them out between the different components of the machine, for example between the fan casing, the main casing and the gas ejection cone of an aircraft engine.

The system comprises means for acquiring 1 at least one acoustic signal supplied by a microphone 7 positioned in the tested machine M and a reference database 5 in which is recorded at least one reference acoustic signature $Sign(R_j)$.

This acquisition makes it possible to form a matrix X of acoustic signals composed of as many lines as microphones, and in which the number of columns depends on the number of samples considered for the analysis. The $i^{th}$ line of the matrix X thus correspond to the different samples of an acoustic signal recorded by a microphone for a given duration. The $j^{th}$ column of the matrix X corresponds to the measurement at a given sampling instant of the signals from the different microphones. Thus, acquired acoustic signal is taken to mean, within the scope of the invention, a set of samples over a time block of a given duration. The invention is implemented over a time block, and may obviously be repeated over other time blocks.

The system moreover comprises a processing chain constituted of a module for separating sources 2, a module for determining an acoustic signature 3 and a module for comparing acoustic signatures 4.

The module for separating sources 2 is more particularly configured to implement a source separation algorithm to separate (break down) at least one acoustic signal into a plurality of sound sources, said signal being modelled as a mixture of components, each one corresponding to a sound source. This algorithm estimates sound sources from measured acoustic signals (also designated observations in the context of source separation).

The acquired acoustic signal(s) are relatively complex in so far as the noise sources are numerous. It may thus be considered that the acoustic signal(s) collect different mixtures of sources. The invention proposes breaking down the mixture(s) acquired by the microphone(s) 7 to produce virtual signals which make it possible to isolate original sound sources.

The module for separating sources 2 may for this purpose be configured so as to carry out a blind separation of sources which is based on a modelling of the signal(s) acquired in the form of a linear mixture of components, each one corresponding to a sound source.

Blind separation of sources makes it possible to extract independent sources from measured signals. In other words, this separation makes it possible to estimate a matrix of sources S and a separation matrix A such that $S=A*X$, where X corresponds to the matrix of acoustic signals acquired. Consequently $X=A^{-1}*S$ where the inverse matrix of the separation matrix A (mixture matrix $A^{-1}$) illustrates the contribution of each of the sources to the formation of each of the acoustic signals, that is to say the weight of each of the components of the acoustic signal corresponding to a source.

In an embodiment, it is considered that the matrix S is of same dimensions as the matrix X, the number of sources thus being equal to the number of measurement channels.

In an embodiment, the blind separation of sources is an ICA (Independent Component Analysis) type separation, for example according to the JADE (Joint Approximate Diagonalization of Eigenmatrices) algorithm. In another embodiment, the blind separation of sources is an SCA (Sparse Component Analysis) type separation.

In an embodiment variant, the system includes a Gabor filter bank arranged upstream of the module for separating sources 2 and configured to apply a discrete Gabor transform to the measured signals, before applying the blind source separation thereto. Gabor filters correspond to pure frequencies modulated by a Gaussian. They are very suited to the recognition of textures on images and may thus be easily exploited on time-frequency representations of the measured signals.

The discrete Gabor transform has the advantage of being reversible and thus to enable not only the analysis of the signal but also the construction of a filter bank (reconstruction of time signals after filtering). The application of this filter bank makes it possible to compensate the low number of sensors and leads to the simulation of several sources corresponding to different textures of the periodogram. The source separation is then applied to the outlets of the filter bank rather than to the source signals.

The module for separating sources 2 may also be configured to carry out a non-blind breakdown. For example, when the number of independent rotating shafts of the engine is known, it is possible using order pursuit methodology to separate the information items stemming from each of the shafts and the noise independent of the rotation speeds.

A non-blind source separation uses the physical configuration of the engine. Generally speaking, the rotation speeds of the shafts and the number of gear blades as well as the definition of anti-friction bearings (diameters and numbers of balls or rollers) mean that it is possible to know in advance the frequencies corresponding to the high pressure body and to the low pressure part. It is thus possible to filter the corresponding frequencies as well as the various modulations. A signal depending uniquely on each shaft may thus be isolated. The same is true of signals for the modulations a priori of each bearing (in amplitude) or gear (in frequency), modulation appearing in the event of defects loaded by an imbalance. The residual signal, after extraction of the isolated signals, may then be processed separately. This residual signal contains notably resonances of casings and noises stemming from the propagation of fluids (hissings) and from the combustion chamber. Some of these resonances may also be filtered when the fundamental modes of the components of the engine are known.

At the end of the step of separation of sources carried out by the module 2, the matrix of sources $$S = \begin{bmatrix} S_1 \\ S_2 \\ \ldots \\ S_N \end{bmatrix}$$

is thus available grouping together on each line the samples of a separated sound source $S_i$. Resorting to these "virtual" sources to carry out a recognition of reference acoustic signatures as described hereafter proves to be advantageous in that, unlike acquired acoustic signals, these sources are independent or practically independent. The recognition of reference acoustic signatures is then more rapid and more reliable.

The module for determining an acoustic signature 3 is for its part more particularly configured to determine at least one characteristic acoustic signature Sign($S_i$) of at least one separated sound source $S_i$. Preferably a characteristic acoustic signature Sign($S_i$) of each of the separated sound sources $S_i$ is determined. In a possible embodiment, one or more of said separated sound sources $S_i$ are considered as being noise not attributable to a specific component of the machine M, and are then not the subject of the determination and comparison of acoustic signatures.

Characteristic signature is taken to mean a unique fingerprint of the source in the form for example of a vector comprising one or more indicators extracted from an analysis, for example a frequency analysis implementing a Fourier transform, of a separated sound source.

The module for comparing acoustic signatures 4 is itself configured to compare the characteristic acoustic signature(s) Sign($S_i$) generated by the module for determining an acoustic signature 3, with the reference acoustic signature(s) Sign($R_j$) recorded in the reference database 5.

These modules 3 and 4 are thus configured to implement a recognition of reference signatures in acoustic signals (here the signals from the separated sources), for example a voice or musical extract recognition method. As an illustrative example, the modules 3 and 4 implement the method described in the article of Wang, Avery Li-Chun entitled "An Industrial-Strength Audio Search Algorithm", Shazam Entertainment, 2003. The module for determining an acoustic signature 3 is then configured to plot a spectrogram of at least one separated source, to identify intensity peaks by thresholding of the spectrogram, and to calculate distances between intensity peaks.

The modules 3 and 4 may also implement a sparse projection method according to which a spectral transformation (spectrogram) of a separated source is projected onto a space of reduced dimension provided with a metric. The projection may be carried out according to a learning projection model carrying out for example a linear regression according to a PCA (Principal Component Analysis) or an NMF (Non-Negative Matrix Factorization), or instead according to a mathematical projection model based for example on curvelet filters.

The result of the recognition of reference signatures may be supplied to a man-machine interface module 6 notably configured to make it possible to notify an operator when a defect of the tested machine M is identified or forecasted.

In a first embodiment illustrated in FIG. 1 carrying out a recognition of signatures of defects, the reference acoustic signature(s) Sign($R_j$) each correspond to an acoustic signature characteristic of a defect of the machine. The module for comparing signatures 4 is then configured to trace a defect signature among the signature(s) of the separated sources. In other words, the module 4 is then configured to carry out the identification of a defect j of the machine when a difference between a characteristic acoustic signature of a separated sound source Sign($S_i$) and the reference acoustic signature characteristic of said defect Sign($R_j$) is below a threshold.

In a possible embodiment, when the identified defect j is confirmed for example via a maintenance inspection, the reference database 5 may be enriched by recording therein the characteristic acoustic signature of a separated sound source Sign($S_i$) close to the reference acoustic signature characteristic of said defect Sign($R_j$). Otherwise, the defect identification threshold may be modified to avoid any false alarm. Furthermore, when a defect occurs, identified in operation or during maintenance for example but not identified by the comparison of acoustic signatures, the acoustic signal of said defect may then be acquired and used to record a reference acoustic signature of said defect in the reference database.

Figure 2:
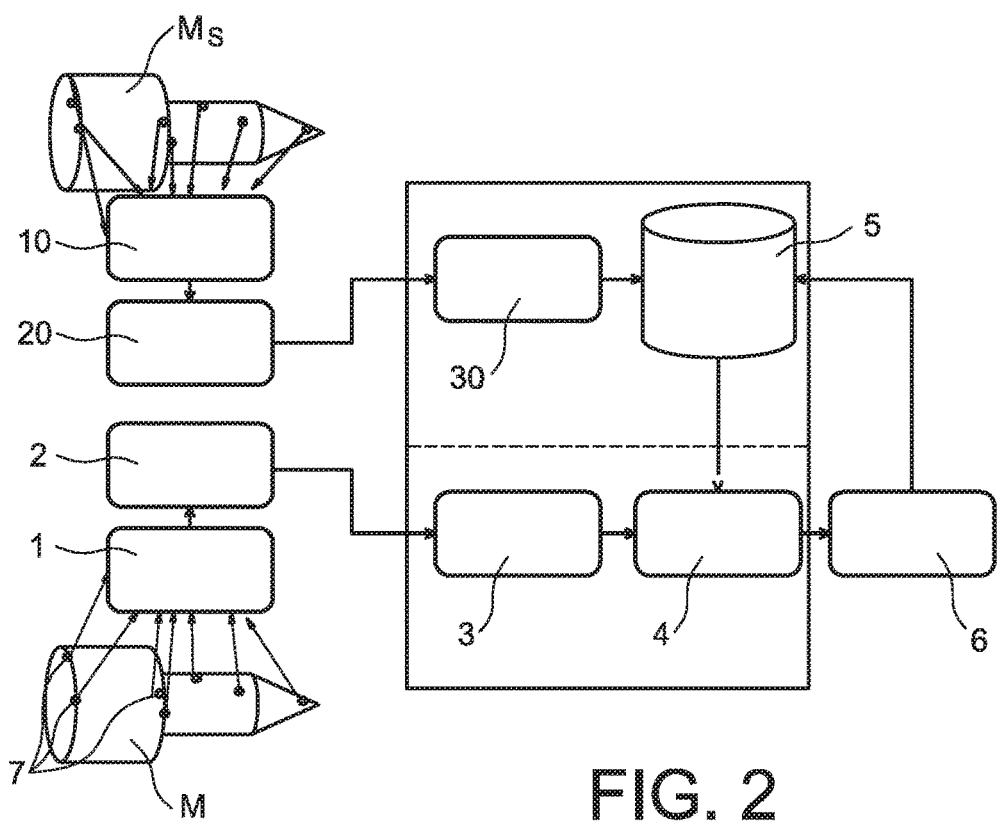
FIG. 2 illustrates in a schematic manner an example of material means implemented in the system or method for the acoustic analysis of a machine according to a second possible embodiment of the invention.
Figure 3:
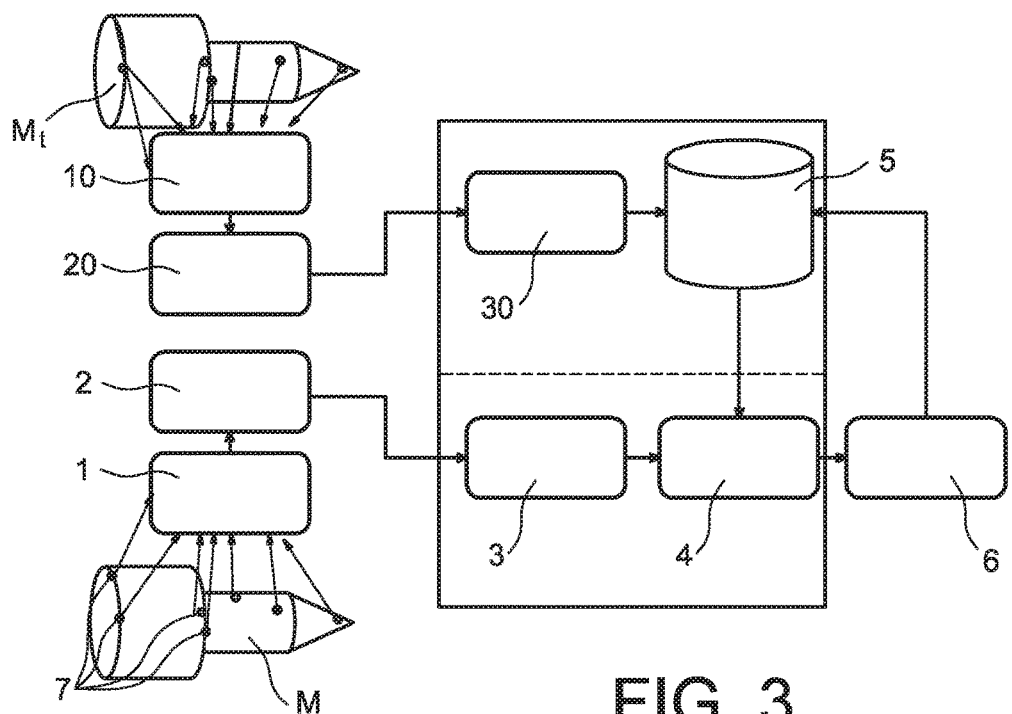
FIG. 3 illustrates in a schematic manner an example of material means implemented in the system or method for the acoustic analysis of a machine according to a third possible embodiment of the invention.
Figure 4:
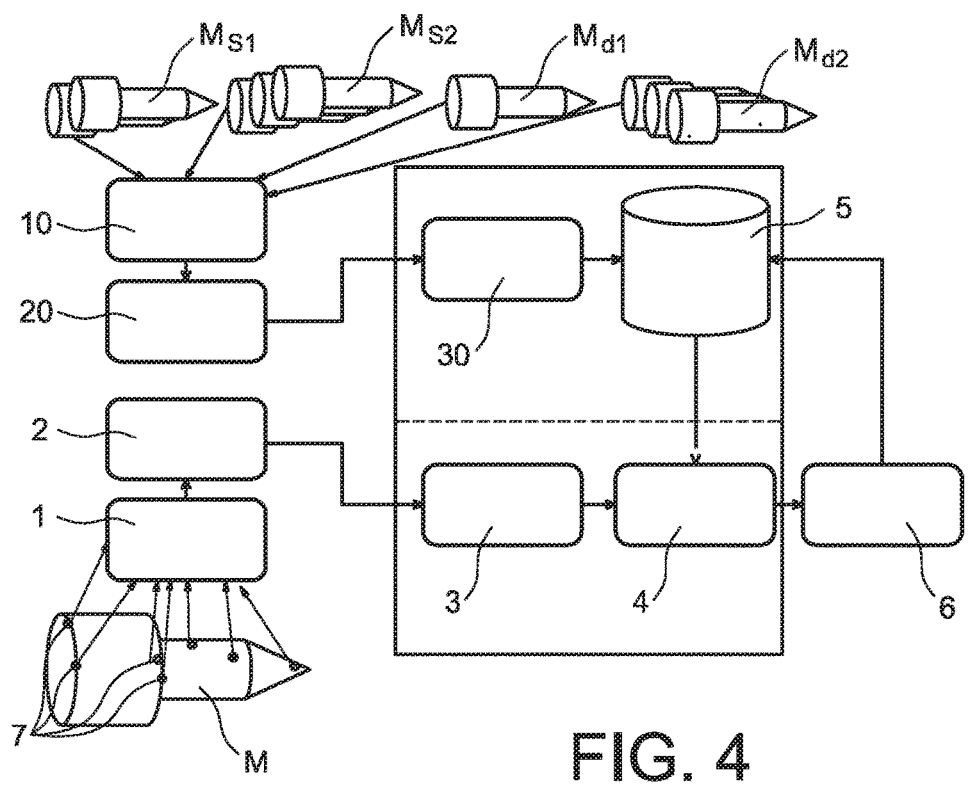
FIG. 4 illustrates in a schematic manner an example of material means implemented in the system or method for the acoustic analysis of a machine according to a fourth possible embodiment of the invention.

In the other embodiments illustrated by FIGS. 2 to 4, a step for determining at least one reference acoustic signature is carried out to complete the reference database 5. This step includes the following operations:

acquisition of at least one reference acoustic signal supplied by a microphone positioned in a reference machine Ms, Mt, Ms, Ms2, Md1, Md2, the microphone(s) preferably being positioned at the same places as the microphone(s) 7 positioned in the tested machine M;

separation of at least one reference acoustic signal into a plurality of reference sound sources Rj using a module for separating sources 20 similar to the module 2 described previously;

for at least one of the separated reference sound sources Rj, preferably for each one of the referenced sound sources attributable to a specific component of the reference machine, determination of a characteristic acoustic signature Sign(Rj) using a module for determining an acoustic signature 30 similar to the module 3 described previously;

recording in the reference database 5 of the characteristic acoustic signature Sign(Rj) of at least one separated reference sound source Rj.

In a second embodiment illustrated by FIG. 2 according to which it is sought to identify a non-recognition of sound signatures, a reference machine in the form of a defect-free machine Ms is considered. In this way one or more signatures characteristic of reference sound sources characterizing a sound operation of the machine are recorded in the reference database 5.

The module for comparing signatures 4 is then configured to check whether for the tested machine M all the signatures characteristic of reference sound sources are found in the characteristic signature(s) of the separate sources: if a reference signature characterizing a sound operation is not found, a defect is identified. In other words, the module 4 is configured to carry out the identification of a defective operation of the tested machine M when a difference between a characteristic acoustic signature of a separated source Sign($S_i$) and an acoustic signature Sign ($R_j$) recorded in the reference database is above a threshold.

In a third embodiment illustrated by FIG. 3 according to which an evolution of the signatures is characterized, the reference machine is the same machine Mt as the tested machine M, considered earlier in time for carrying out the step for determining reference acoustic signatures, on leaving the factory for example while it is known that the machine Mt is not defective or during the operation of the machine, for example at the end of a certain number of flights.

The module for comparing signatures 4 is then configured to calculate an overall difference between the signature(s) of the sources of the tested machine M with the signature(s) of the sources of the reference machine Mt. This difference makes it possible to characterize a potential degradation of the engine from the carrying out of the prior step of determination of reference acoustic signatures. In other words, the module 4 is here configured to carry out the identification of a defective operation of the machine when a difference between a fingerprint vector of the machine composed of the characteristic acoustic signature(s) of the separated sources Sign(Si) and a fingerprint vector composed of the acoustic signature(s) recorded in the reference database Sign(Rj) is above a threshold.

In a variant of this third embodiment, the reference machine Mt is a machine of the same type as the tested machine M having the same operating history. The reference machine Mt and the tested machine M are for example the engines of a same aircraft.

In a fourth embodiment illustrated by FIG. 4, resort is made to several reference machines, the objective being to identify which of the reference machines is the closest to the tested machine.

The reference machines may include one or more defect-free machines Ms1, Ms2, as well as one or more defective machines Md1, Md2 that can be grouped together into classes according to the type of anomaly (for example a class of defective turbine engines and another class of defective compressor engines). The classes may be defined by experts in the analysis of the noise generated by the machine (analysis based on their job expertise or instead on an analysis of a set of spectrograms already determined for comparable machines, available in a reference database, analysis based on an identification by the expert of identical zones in the spectrograms). The classes may also be defined using automatic classification tools, implementing for example a hierarchical classification, a Gaussian mixture model (for example via the expectation-maximization algorithm), or instead a self-organizing map, etc.

The module for comparing signatures 4 is here configured to calculate, for each reference machine or each class of reference machines, the difference between a fingerprint vector of the tested machine composed of the characteristic acoustic signature(s) of the separated sources and a fingerprint vector composed of the acoustic signature(s) recorded in the reference database corresponding to the reference machine or to the class of reference machines. The smallest difference indicates the reference machine, or the class of reference machines, the closest to the tested machine. If the reference machine is a defective machine, or if the class of reference machines is a class representative of an anomaly, an alert of defective operation may be emitted by the man-machine interface module 6. In a possible embodiment, when the difference between the fingerprint vector of the tested machine and each of the reference fingerprint vectors is above a threshold, it is considered that the tested machine is defective and a new class is created with the tested machine.

In the embodiments of FIGS. 2-4, when a defect of the tested machine is identified, but that said defect is not confirmed for example via a maintenance inspection, the defect identification threshold may be modified to avoid any false alarm.

The invention is not limited to the system and method as described previously, but also extends to a computer program product including code instructions for the execution of the steps of the method according to the invention when said program is run on a computer.

What is claimed is:

1. A method of monitoring an aircraft engine comprising:
    acquiring at least one acoustic signal supplied by at least one microphone positioned in the aircraft engine;
    performing non-blind source separation on the at least one acquired acoustic signal so as to separate the at least one acquired acoustic signal into a plurality of sound sources, said at least one acquired acoustic signal being modelled as a mixture of components, each one corresponding to a sound source;
    for at least one of the separated sound sources, determining a characteristic acoustic signature;
    comparing the at least one characteristic acoustic signature with at least one reference acoustic signature recorded in a reference database; and
    detecting a defect of the aircraft engine based on a result of the comparison,
wherein performing the non-blind source separation on the at least one acquired acoustic signal comprises:
    determining at least one residual signal by filtering the at least one acquired acoustic signal to remove frequencies corresponding to known resonances of components of the engine, and
    performing source separation on the at least one residual signal based on a modelling of the at least one residual signal as a mixture of independent sound sources, thereby estimating each one of the independent sound sources from the at least one residual signal.

2. The method according to claim 1, wherein each reference acoustic signature corresponds to an acoustic signature characteristic of a defect of the aircraft engine, and the defect of the aircraft engine is detected when a difference between a characteristic acoustic signature of a separated sound source and the reference acoustic signature characteristic of said defect is below a threshold.

3. The method according to claim 1, further comprises determining at least one reference acoustic signature which comprises:
    an acquisition of at least one reference acoustic signal supplied by at least one microphone positioned in at least one reference aircraft engine;
    a separation of at least one reference acoustic signal into a plurality of reference sound sources;
    for at least one of the separated reference sound sources, a determination of a reference acoustic signature;
    a recording in the reference database of the reference acoustic signature of at least one separated reference sound source.

4. The method according to claim 3, wherein at least one reference aircraft engine is a defect-free aircraft engine, and the defect of the aircraft engine is detected when a difference between a characteristic acoustic signature of a separated sound source and an acoustic signature recorded in the reference database is above a threshold.

5. The method according to claim 4, wherein at least one reference aircraft engine includes at least two aircraft engines, said method including a calculation of differences between a fingerprint vector of the aircraft engine under acoustic analysis composed of at least one characteristic acoustic signature of at least one separated sound source and fingerprint vectors each constituted of at least one reference acoustic signature recorded in the reference database corresponding to one of the reference aircraft engines.

6. The method according to claim 3, wherein at least one reference aircraft engine is the same aircraft engine as the aircraft engine under acoustic analysis considered earlier or an aircraft engine of the same type having the same operating history, and the defect of the aircraft engine is detected when a difference between a fingerprint vector of the aircraft engine composed of at least one characteristic acoustic signature of at least one separated sound source and a fingerprint vector composed of at least one reference acoustic signature recorded in the reference database is above a threshold.

7. The method according to claim 1, wherein the determination of a characteristic acoustic signature of a separated sound source includes a plotting of a spectrogram of said separated sound source, an identification of intensity peaks by thresholding of the spectrogram, a calculation of distances between said intensity peaks.

8. The method according to claim 1, wherein the non-blind source separation of the at least one acquired acoustic signal into a plurality of sound sources is carried out by a computer processor configured to implement an independent component analysis.

9. A non-transitory computer-readable medium having stored thereon a program product including code instructions for the execution of the steps of the method according to claim 1, when said program is run on a computer.

10. The method according to claim 1, wherein the non-blind source separation comprises filtering, from the at least one acoustic signal, previously known resonances of components of the aircraft engine.

11. The method according to claim 1, further comprising, prior to performing non-blind source separation on the at least one acoustic signal, a step of filtering the at least one acquired acoustic signal with a bank of Gabor filters.

12. A system for the acoustic analysis of an aircraft engine, including means for acquiring at least one acoustic signal supplied by at least one microphone positioned in the aircraft engine, and a reference database in which is recorded at least one reference acoustic signature, the system further comprising:
 a module for performing non-blind source separation on the at least one acoustic signal so as to separate the at least one acoustic signal into a plurality of sound sources, said at least one acoustic signal being modelled as a mixture of components each one corresponding to a sound source;
 a module for determining an acoustic signature configured to determine at least one characteristic acoustic signature of at least one of the separated sound source;
 a module for comparing acoustic signatures configured to compare at least one characteristic acoustic signature with at least one reference acoustic signature recorded in the reference database; and
 a module for detecting a defect of the aircraft engine based on a comparison result provided by the module for comparing,
wherein performing the non-blind source separation on the at least one acoustic signal comprises:
 determining at least one residual signal by filtering the at least one acoustic signal to remove frequencies corresponding to known resonances of components of the engine, and
 performing source separation on the at least one residual signal based on a modelling of the at least one residual signal as a mixture of independent sound sources, thereby estimating each one of the independent sound sources from the at least one residual signal.

* * * * *